(12) United States Patent
Grafton

(10) Patent No.: US 6,994,719 B2
(45) Date of Patent: Feb. 7, 2006

(54) HIGH STRENGTH SUTURE WITH COLORED TRACE AT ONE END

(75) Inventor: R. Donald Grafton, Naples, FL (US)

(73) Assignee: Arthrex, Inc., Naples, FL (US)

(*) Notice: Subject to any disclaimer, the term of this patent is extended or adjusted under 35 U.S.C. 154(b) by 41 days.

(21) Appl. No.: 10/358,399

(22) Filed: Feb. 5, 2003

(65) Prior Publication Data

US 2003/0139775 A1    Jul. 24, 2003

Related U.S. Application Data

(63) Continuation-in-part of application No. 10/160,176, filed on Jun. 4, 2002, which is a continuation-in-part of application No. 09/950,598, filed on Sep. 13, 2001, now Pat. No. 6,716,234.

(60) Provisional application No. 60/330,913, filed on Nov. 2, 2001, provisional application No. 60/350,040, filed on Jan. 23, 2002, provisional application No. 60/354,499, filed on Feb. 8, 2002.

(51) Int. Cl.
*A61B 17/04* (2006.01)

(52) U.S. Cl. ............................ 606/228; 606/230

(58) Field of Classification Search ............ 606/228, 606/230, 232
See application file for complete search history.

(56) References Cited

U.S. PATENT DOCUMENTS

| 3,942,532 A | 3/1976 | Hunter et al. |
| 3,949,755 A | 4/1976 | Vauquois |
| 4,047,533 A | 9/1977 | Perciaccante et al. |
| 4,344,908 A | 8/1982 | Smith et al. |
| 4,411,854 A | 10/1983 | Maurer et al. |
| 4,422,993 A | 12/1983 | Smith et al. |
| 4,430,383 A | 2/1984 | Smith et al. |
| 4,436,689 A | 3/1984 | Smith et al. |
| 4,668,717 A | 5/1987 | Lemstra et al. |
| 5,019,093 A | 5/1991 | Kaplan et al. |
| 5,067,538 A | 11/1991 | Nelson et al. |
| 5,123,528 A * | 6/1992 | Brown et al. ............... 206/63.3 |
| 5,234,764 A | 8/1993 | Nelson et al. |
| 5,261,886 A | 11/1993 | Chesterfield et al. |
| 5,314,446 A | 5/1994 | Hunter et al. |

(Continued)

FOREIGN PATENT DOCUMENTS

EP    0 561 108 A2    9/1993

*Primary Examiner*—Gary Jackson
(74) *Attorney, Agent, or Firm*—Dickstein Shapiro Morin & Oshinsky LLP

(57) ABSTRACT

A high strength abrasion resistant surgical suture material with improved tie down characteristics is color coded for visualization and identification purposes. The suture features a multifilament cover formed of strands of ultra high molecular weight long chain polyethylene braided with polyester, nylon or a bioabsorbable material. Selected nylon fibers in the cover are provided in a color contrasting with the other cover fibers to provide an identifiable trace. The cover surrounds a core formed of twisted strands of ultra-high molecular weight polyethylene. The suture, provided in a #2 size, has the strength of #5 Ethibond, is ideally suited for most orthopedic procedures, and can be attached to a suture anchor or a curved needle. The identifiable trace preferably is provided along one half of the length of the suture, so that when the suture is loaded onto a suture anchor, for example, the two legs of the length of suture on either side of the suture anchor can be readily identified.

20 Claims, 3 Drawing Sheets

U.S. PATENT DOCUMENTS

| | | |
|---|---|---|
| 5,318,575 A | 6/1994 | Chesterfield et al. |
| 5,383,925 A | 1/1995 | Schmitt |
| 5,403,659 A | 4/1995 | Nelson et al. |
| 5,540,703 A | 7/1996 | Barker, Jr. et al. |
| 5,573,529 A * | 11/1996 | Haak et al. .................. 606/1 |
| 5,630,976 A | 5/1997 | Nelson et al. |
| 5,720,765 A | 2/1998 | Thal |
| 6,029,806 A * | 2/2000 | Cerwin et al. ............. 206/63.3 |
| 6,045,571 A | 4/2000 | Hill et al. |
| 6,063,105 A | 5/2000 | Totakura |

* cited by examiner

HIGH STRENGTH SUTURE WITH COLORED TRACE AT ONE END

CROSS-REFERENCE TO RELATED APPLICATIONS

This application is a continuation-in-part of U.S. patent application Ser. No. 10/160,176 filed on Jun. 4, 2002, which is a continuation-in-part of U.S. patent application Ser. No. 09/950,598 filed Sep. 13, 2001, now U.S. application Ser. No. 6,716,234 and claims the benefit of the following: U.S. provisional application Ser. No. 60/330,913 filed Nov. 2, 2001, U.S. provisional application Ser. No. 60/350,040, filed Jan. 23, 2002, and U.S. provisional application Ser. No. 60/354,499 filed Feb. 8, 2002.

BACKGROUND OF THE INVENTION

1. Field of the Invention

The present invention relates to high strength surgical suture materials, and more particularly to braided suture blends of ultrahigh molecular weight polyethylene having coatings to improve handling, and colored strands for tracing and identifying the suture.

2. Description of the Related Art

Suture strength is an important consideration in any surgical suture material. One of the strongest materials currently formed into elongated strands is an ultrahigh molecular weight long chain polyethylene, typically used for fishing line and the like, which is sold under the trade names Dyneema or Spectra. This material is much stronger than ordinary surgical suture, however, it does not have acceptable knot tie down characteristics for use in surgical applications.

BRIEF SUMMARY OF THE INVENTION

The present invention advantageously provides a high strength surgical suture material with improved tie down characteristics. The suture features a braided cover made of a blend of ultrahigh molecular weight long chain polyethylene fiber and a fiber of one or more long chain synthetic polymers, preferably polyester. The polyethylene provides strength. The polyester provides improved tie down properties.

Handling properties of the high strength suture also are enhanced using various materials to coat the suture. In addition, strands of a contrasting color are added to the braided threads to enhance visibility. The colored strands preferably are dyed filaments of polyester or nylon. In an exemplary embodiment, half of a length of suture is provided with colored tracing strands, or otherwise contrasts with the other half of the length of suture, which remains a plain, solid color, for example. Accordingly, when the length of suture is loaded through the eyelet of a suture anchor, for example, identification and movement of the suture legs is simplified. The half-trace/half-plain arrangement of the suture facilitates tracing and identification of the two legs of the suture during arthroscopic surgery.

In a preferred embodiment, the suture includes a multifilament cover formed of ultrahigh molecular weight polyethylene fiber braided with polyester and nylon fibers. The cover surrounds a fiber core substantially or entirely of ultrahigh molecular weight polyethylene. The core preferably comprises 3 strands of ultrahigh molecular weight polyethylene, twisted at about 3 to 6 twists per inch.

The cover preferably comprises 8 strands of ultrahigh molecular weight polyethylene braided with 6 strands of polyester and 2 strands of nylon, the nylon strands being provided in black or some other contrasting color as explained in greater detail below.

Ultrahigh molecular weight polyethylene fibers suitable for use in the present invention are marketed under the Dyneema trademark by Toyo Boseki Kabushiki Kaisha, and are produced in the U.S. by Honeywell under the trademark Spectra.

The suture of the present invention advantageously has the strength of Ethibond #5 suture, yet has the diameter, feel and tie ability of #2 suture. As a result, the suture of the present invention is ideal for most orthopedic procedures such as rotator cuff repair, Achilles tendon repair, patellar tendon repair, ACL/PCL reconstruction, hip and shoulder reconstruction procedures, and replacement for suture used in or with suture anchors.

The suture can be uncoated, or coated with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, or abrasion resistance, for example.

As an added advantage, as mentioned above, all or some of the nylon fibers (or the polyester fibers) in the cover are provided in a contrasting color for visibility and identification purposes. A few trace threads having a contrasting color, preferably of a readily dyed fiber such as polyester or nylon, in the cover aid surgeons in identifying the travel direction of the suture during surgery, particularly during arthroscopic operations. Providing the trace threads in a regularly repeating pattern is particularly useful, allowing the surgeon to distinguish different ends of lengths of suture, and determine the direction of travel of a moving length of suture. The trace threads preferably are provided on only half of a length of suture to allow for tracing and identification of the two halves of the suture, such as when the suture is threaded through an eyelet of a suture anchor. Of the more easily dyed fibers, nylon is preferred in that it accepts dye readily. Polyester fibers are stronger, but do not take up dye as easily as nylon.

Other features and advantages of the present invention will become apparent from the following description of the invention which refers to the accompanying drawings.

DETAILED DESCRIPTION OF THE INVENTION

Figure 1:
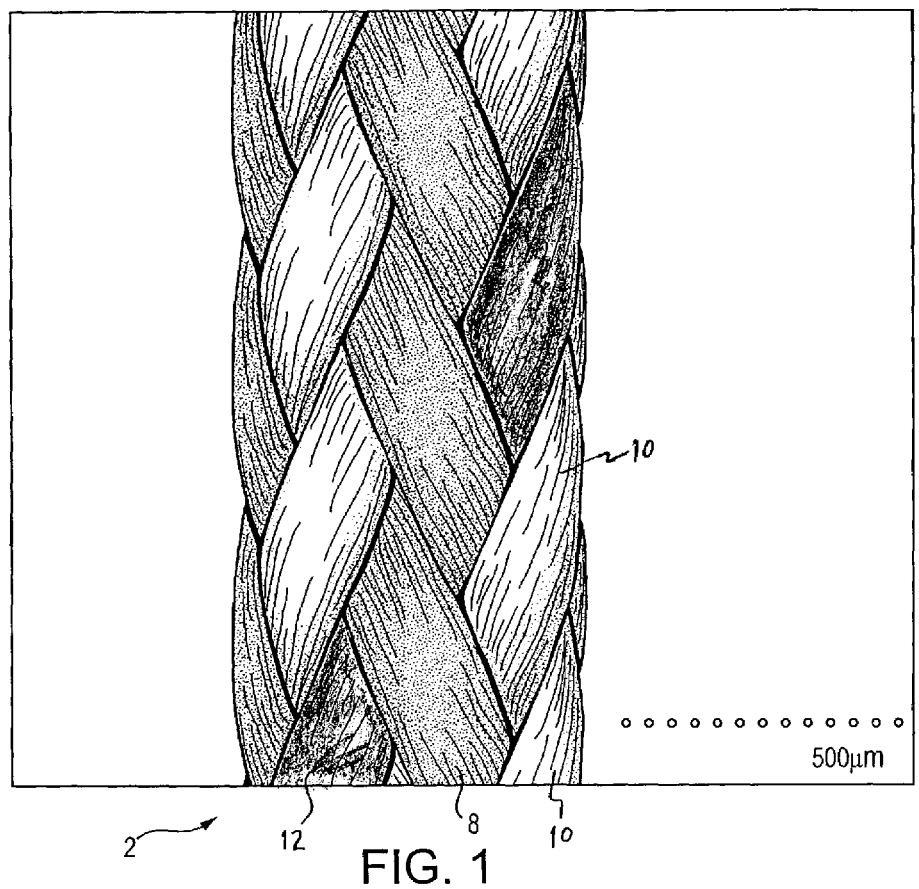
FIG. 1 is a copy of a scanning electron micrograph of a length of suture according to the present invention.
Figure 2:
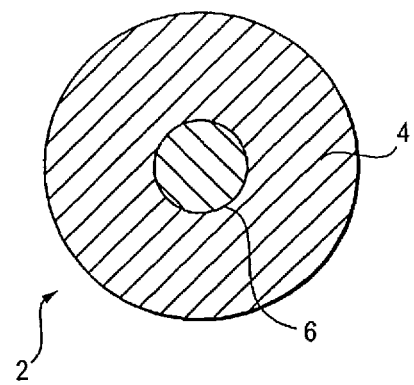
FIG. 2 is a schematic cross section of a length of suture according to the present invention.

Referring to FIG. 1, a scanning electron micrograph of a length of suture 2 according to the present invention is shown. Suture 2 is made up of a cover 4 and a core 6 surrounded by the cover. See FIG. 2. Strands of ultrahigh molecular weight polyethylene (UHMWPE) 8, sold under the tradename Spectra or Dyneema, and strands of polyester 10 and 12 are braided together to form the cover 4. Core 6 is formed of twisted strands of UHMWPE.

UHMWPE strands 8 are substantially translucent or colorless. The majority of the polyester strands 10 are white (undyed), with one or more additional polyester or nylon strands 12 having a contrasting color provide a trace in the suture. Due to the transparent nature of the UHMWPE, the suture takes on the color of strands 10 and 12, and thus appears to be white with a trace in the contrasting color.

In accordance with the present invention, trace strands 12 are preferably provided in black. The black trace assists the surgeon in differentiating between suture strands with the trace and suture strands without the trace. The trace also assists the surgeon in identifying whether the suture is moving. More preferably, the trace is provided on half of a length of suture, the other half of the length of suture remaining plain. Accordingly, when the suture is threaded through the eyelet of a suture anchor, for example, the two legs of the length of suture easily are distinguished, and their direction of travel becomes more evident as well.

Details of the present invention will be described further below in connection with the following examples:

EXAMPLE

USP Size 5 (EP size 7)

Made on a 16 carrier Hobourns machine, the yarns used in the braided cover are Honeywell Spectra 2000, polyester type 712, and nylon. The cover is formed using eight strands of 144 decitex Spectra per carrier, braided with six strands of 100 decitex polyester, and two strands of colored nylon. The core is formed of three carriers of 144 decitex Spectra braided at three to six twists per inch.

The example set forth above is for size 5 suture. In the making of various sizes of the inventive suture, different decitex values and different PPI settings can be used to achieve the required size and strength needed. In addition, smaller sizes may require manufacture on 12 carrier machines, for example. The very smallest sizes preferably are made without a core. Overall, the suture may range from 5% to 90% ultrahigh molecular weight polymer (preferably at least 40% of the fibers are ultrahigh molecular weight polymer), with the balance formed of polyester and/or nylon. The core preferably comprises 18% or greater of the total amount of filament.

The suture preferably is coated with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, or abrasion resistance, for example.

The ultra high molecular weight (UHMW) polymer component of the present invention provides strength, and the polyester component is provided to improve tie ability and tie down characteristics. However, it has been found that the UHMW polymer provides an unexpected advantage of acting as a cushion for the polyester fibers, which are relatively hard and tend to damage each other. The UHMW polymer prevents breakage by reducing damage to the polyester when the suture is subjected to stress.

According to an alternative embodiment of the present invention, a partially bioabsorbable suture is provided by blending a high strength material, such as UHMWPE fibers, with a bioabsorbable material, such as PLLA or one of the other polylactides, for example. Accordingly, a suture made with about 10% Spectra or Dyneema blended with absorbable fibers would provide greater strength than existing bioabsorbable suture with less stretch. Over time, 90% or more of the suture would absorb, leaving only a very small remnant of the knot. The absorbable suture can include coatings and colored traces as noted above for nonabsorbable suture.

Figure 3:
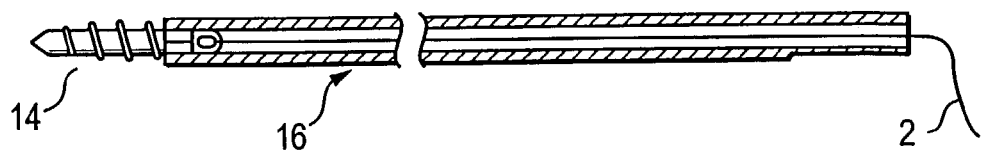
FIG. 3 is an illustration of the suture of the present invention attached to a suture anchor.
Figure 4A:
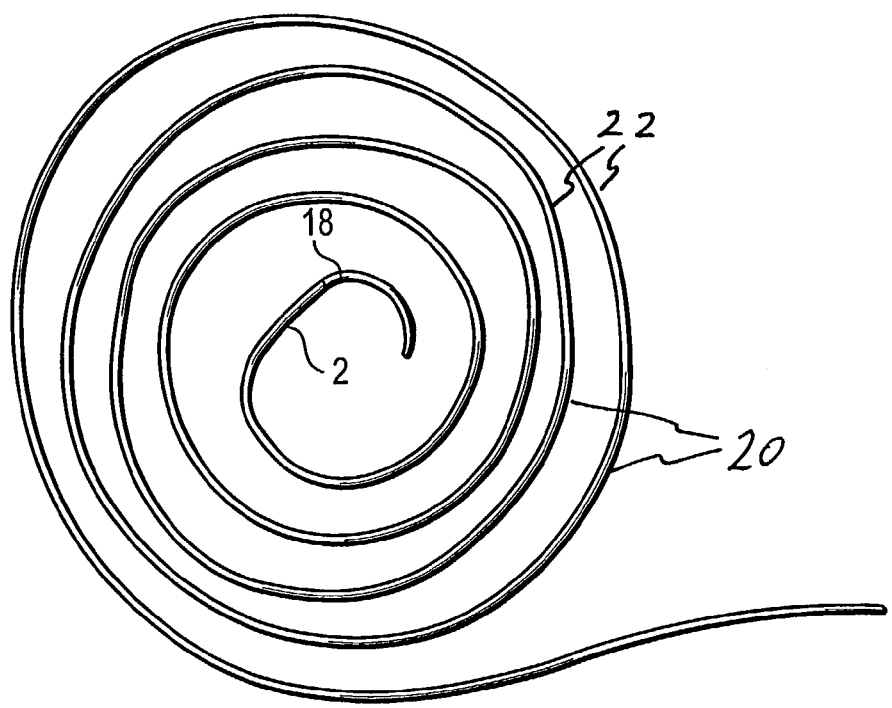
FIGS. 4A and 4B show the suture of the present invention attached to a half round, tapered needle.
Figure 4B:
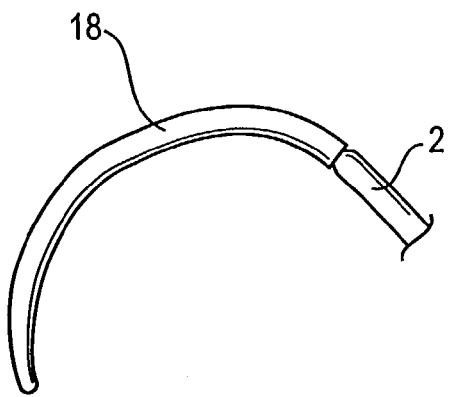

In one method of using the suture of the present invention, the suture 2 is attached to a suture anchor 14 as shown in FIG. 3 (prepackaged sterile with an inserter 16), or is attached at one or both ends to a half round, tapered needle 18 as shown in FIGS. 4A and 4B. FIG. 4A also illustrates a length of suture having regularly repeating pattern of trace threads according to the present invention. Sections 20 of the length of suture 2 have tracing threads woven in, where sections 22 of the length of suture are plain, or otherwise are distinguishable from sections 20. The alternating patterned and plain sections aid the surgeon in determining the direction of suture travel, for example.

Figure 6:
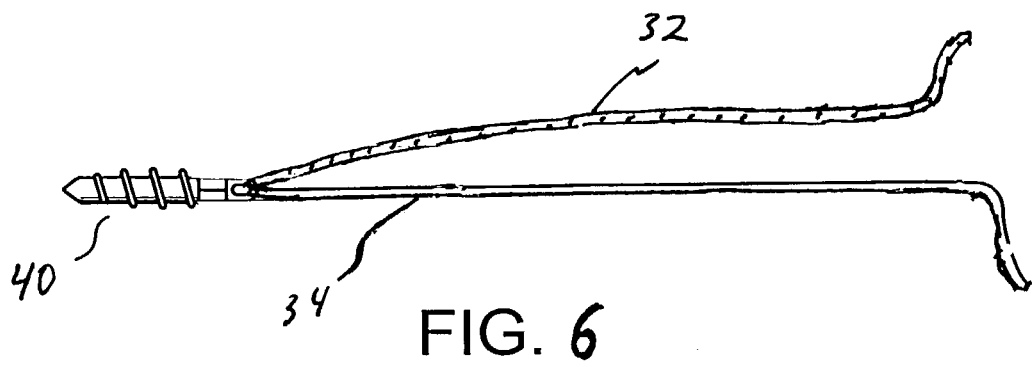
FIG. 6 illustrates a strand of suture according to the present invention provided on a suture anchor.
Figure 5:
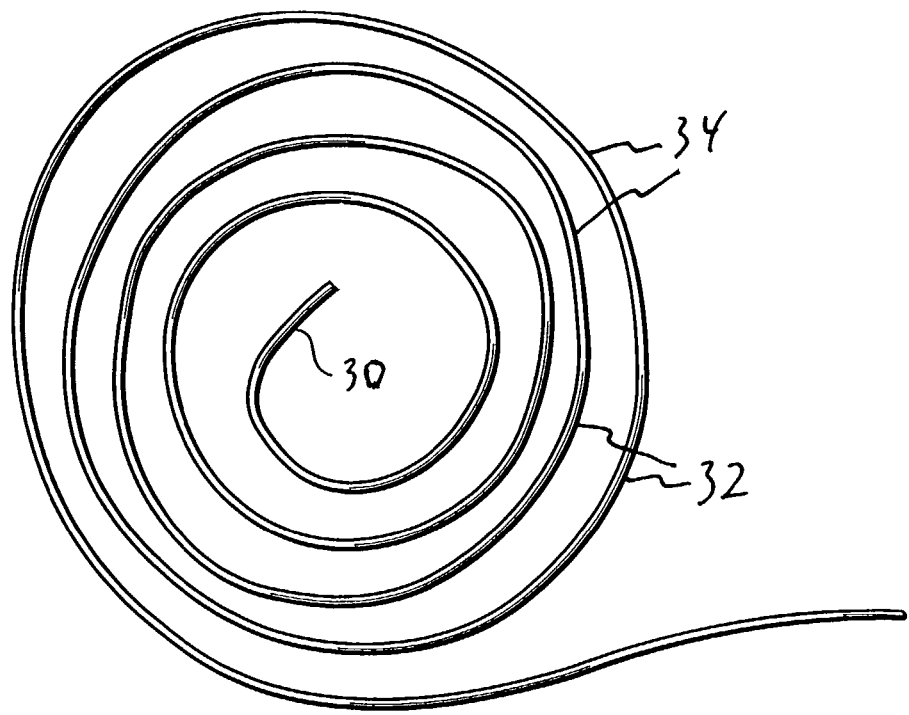
FIG. 5 illustrates a bulk length of suture of the present invention.

As shown in FIG. 5, bulk suture 30 is provided with repeating sections 32 having trace threads separated by sections 34 having no trace threads. The bulk suture is cut between every other section, at one end of each plain section, for example, to provide lengths of suture that are half traced and half plain. Alternatively, the bulk suture can be cut midway through each section to provide a shorter suture having a trace at one end. The half-and-half lengths of suture can be threaded through the eyelet of a suture anchor 40, as shown in FIG. 6. Accordingly, each leg of the suture strand provided on the suture anchor is easily distinguishable by a surgeon operating with the suture anchor assembly.

As set forth in Example 1 as described above, one or more strands of a fiber in the blend can be provided in pre-dyed colors, e.g., black, to provide a trace. The trace threads enhance the ability to visually detect suture motion and the ability to differentiate between colored and uncolored suture strands.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A suture strand suitable for use as a suture or ligature comprising a plurality of braided fibers of ultrahigh molecular weight polyethylene, and a plurality of fibers of at least one long chain synthetic polymer or bioabsorbable fiber, the fibers being combined to produce the suture strand, sections of at least one of the plurality of fibers being provided in a color contrasting from the other fibers to provide an identifiable trace along a longitudinal portion of the suture strand which is less than an entire length of the suture stand, at least one other longitudinal portion of the suture strand being provided with no identifiable trace.

2. The suture strand of claim 1, wherein the longitudinal portion of the suture provided with no identifiable trace is disposed at one end of the suture strand and the longitudinal portion provided with the identifiable trace is disposed at the other of the suture strand.

3. The suture strand of claim 1, wherein the strand includes only two longitudinal portions, one longitudinal portion of the suture provided with no identifiable trace and the other longitudinal portion being provided with the identifiable trace.

4. The suture strand of claim 3, wherein each longitudinal portion represents a half length of the strand.

5. The suture strand of claim 1, wherein the at least one long chain synthetic polymer is polyester, nylon, or both.

6. The suture strand of claim 1, wherein the ultrahigh molecular weight polyethylene comprises at least 40% of the braided fibers.

7. The suture strand of claim 1, wherein the polyester comprises less than about 40% of the braided filaments.

8. The suture strand of claim 1, further comprising a core of twisted fibers of ultrahigh molecular weight polyethylene surrounded by a cover comprising the plurality of braided fibers of ultrahigh molecular weight polyethylene and polyester.

9. The suture strand of claim 8, wherein the core comprises about 18% or greater of the total amount of filament.

10. The suture strand of claim 8, wherein the cover comprises less than about 82% of the total amount of filament.

11. The suture strand of claim 8, further comprising a coating disposed on the cover.

12. The suture strand of claim 11, wherein the coating is selected from the group consisting of wax, silicone, silicone rubbers, PTFE, PBA, and ethyl cellulose.

13. A suture assembly comprising:
a suture having a longitudinal length and a multifilament cover formed of a plurality of braided fibers of ultrahigh molecular weight polyethylene and fibers of polyester, nylon, bioabsorbable material or a combination thereof, at least one of the fibers of polyester, nylon or bioabsorbable material being provided in a color contrasting with the remaining fibers on substantially only one half of the longitudinal length of the suture, and a core formed of twisted fibers of ultrahigh molecular weight polyethylene; and
a suture anchor attached to the suture.

14. A suture assembly comprising:
a suture having a longitudinal length and a multifilament cover formed of a plurality of braided fibers of ultrahigh molecular weight polyethylene and fibers of polyester, nylon, bioabsorbable material or a combination thereof, at least one of the fibers of polyester, nylon or bioabsorbable material being provided in a color contrasting with the remaining fibers along only one half of the longitudinal length of suture, and a core formed of twisted fibers of ultrahigh molecular weight polyethylene; and
a half round, tapered needle attached to one or both ends of the suture.

15. A suture strand suitable for use as a suture or ligature having a longitudinal length and at least an outer cover comprising a plurality of braided fibers, at least one of the fibers being colored to provide an identifiable trace along substantially only one half of the longitudinal length of the suture strand.

16. The suture strand of claim 15, wherein the coating is selected from the group consisting of wax, silicone, silicone rubbers, PTFE, PBA, and ethyl cellulose.

17. A method of making suture comprising the steps of:
forming a bulk length of multifilament suture material having alternating sections, every other section being distinguished by an identifiable trace; and
cutting the bulk length into sections, each section having only one end containing the identifiable trace.

18. The method of claim 17, wherein the identifiable trace is provided by weaving into the suture at least one thread having a contrasting color from the rest of the suture material.

19. The method of claim 17, wherein the step of cutting comprises severing the bulk length of suture at a beginning of every other section.

20. The method of claim 17, wherein the step of cutting comprises severing the bulk length of suture at about the midpoint of every section.

* * * * *